United States Patent
Spiegel et al.

(10) Patent No.: US 11,737,706 B2
(45) Date of Patent: Aug. 29, 2023

(54) METHODS FOR OPTIMIZING THE TIMING OF FOOD INGESTION THROUGH MONITORING OF ACOUSTICAL ACTIVITY OF THE ABDOMINAL REGION

(71) Applicant: Cedars-Sinai Medical Center, Los Angeles, CA (US)

(72) Inventors: Brennan Spiegel, Los Angeles, CA (US); Christopher Almario, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 802 days.

(21) Appl. No.: 16/610,426

(22) PCT Filed: May 2, 2018

(86) PCT No.: PCT/US2018/030678
§ 371 (c)(1),
(2) Date: Nov. 1, 2019

(87) PCT Pub. No.: WO2018/204511
PCT Pub. Date: Nov. 8, 2018

(65) Prior Publication Data
US 2021/0186415 A1    Jun. 24, 2021

Related U.S. Application Data

(60) Provisional application No. 62/500,771, filed on May 3, 2017.

(51) Int. Cl.
*A61B 5/00* (2006.01)
*A61B 7/00* (2006.01)
*G06N 5/04* (2023.01)

(52) U.S. Cl.
CPC ............ *A61B 5/486* (2013.01); *A61B 5/4255* (2013.01); *A61B 5/742* (2013.01); *A61B 7/008* (2013.01);
(Continued)

(58) Field of Classification Search
CPC ....... A61B 5/486; A61B 5/4255; A61B 5/742; A61B 5/68335; A61B 7/008; G06N 5/04
See application file for complete search history.

(56) References Cited

U.S. PATENT DOCUMENTS

| 5,301,679 A | 4/1994 | Taylor |
| 10,993,692 B2 | 5/2021 | Spiegel |

(Continued)

FOREIGN PATENT DOCUMENTS

| CN | 105758949 A | 7/2016 |
| WO | 2014039404 A1 | 3/2014 |

(Continued)

OTHER PUBLICATIONS

A. Jain, K. Nandakumarand A. Ross, "Score normalization in multimodal biometric systems", Pattern Recognition, vol. 38, No. 12, pp. 2270-2285, 2005. Available: 10.1016/j.patcog.2005.01.012 (Year: 2005).*

(Continued)

*Primary Examiner* — Lynsey C Eiseman
*Assistant Examiner* — Amanda L Steinberg
(74) *Attorney, Agent, or Firm* — Nixon Peabody LLP

(57) ABSTRACT

Described herein are methods and systems for monitoring acoustical activity from the abdominal region to guide the optimal timing of food ingestion. According to one embodiment of the method, the rate of intestinal digestion events, as well as the change in the rate across specific time periods, is analyzed to guide ingestion behavior in a way that improves health. The result of guidance may be to reduce weight in (Continued)

people who are obese, to improve performance in athletes seeking to balance energy availability and energy expenditure, or to increase caloric intake in people who are undernourished. The method can be applied using a smartphone application to provide contextually appropriate and specific user guidance about whether, when, and how much to eat in a manner that aligns with the physiologic patterns of intestinal activity.

19 Claims, 9 Drawing Sheets

(52) U.S. Cl.
CPC ............ *G06N 5/04* (2013.01); *A61B 5/68335* (2017.08); *A61B 2560/0223* (2013.01)

(56) References Cited

U.S. PATENT DOCUMENTS

| | | |
|---|---|---|
| 2002/0156398 A1 | 10/2002 | Mansy et al. |
| 2003/0153847 A1 | 8/2003 | Sandler et al. |
| 2006/0199155 A1 | 9/2006 | Mosher |
| 2007/0238995 A1 | 10/2007 | Sui et al. |
| 2008/0306355 A1 | 12/2008 | Walker |
| 2010/0228105 A1 | 9/2010 | Policker et al. |
| 2011/0056264 A1 | 3/2011 | Kaplan et al. |
| 2011/0257490 A1 | 10/2011 | Semier |
| 2011/0276312 A1* | 11/2011 | Shalon ................... A61B 5/11 73/488 |
| 2012/0116186 A1 | 5/2012 | Shrivastav et al. |
| 2013/0035610 A1 | 2/2013 | Cromwell |
| 2013/0324804 A1* | 12/2013 | McKeown .............. G16Z 99/00 600/300 |
| 2014/0348370 A1 | 11/2014 | Huang et al. |
| 2015/0250445 A1 | 9/2015 | Spiegel et al. |
| 2017/0055871 A1 | 3/2017 | Axelrod et al. |
| 2018/0242908 A1* | 8/2018 | Sazonov .............. A61B 5/7278 |
| 2018/0333133 A1 | 11/2018 | Spiegel |

FOREIGN PATENT DOCUMENTS

| | | | |
|---|---|---|---|
| WO | WO-2015073878 A1 * | 5/2015 | ....... G01N 33/54366 |
| WO | 2016112127 A1 | 7/2016 | |
| WO | WO-2016112127 A1 * | 7/2016 | ............. A61B 5/002 |
| WO | 2017099816 A1 | 6/2017 | |
| WO | 2018204511 A1 | 11/2018 | |

OTHER PUBLICATIONS

International Search Report and Written Opinion of International Application No. PCT/US2018/030678, dated Jul. 19, 2018 (12 pages).
Extended European Search Report for Application No. EP 16783485. 3, dated Jul. 23, 2019 (10 pages).
International Search Report and Written Opinion of PCT/US2016/ 000120, dated Mar. 16, 2017 (8 Pages).

* cited by examiner

METHODS FOR OPTIMIZING THE TIMING OF FOOD INGESTION THROUGH MONITORING OF ACOUSTICAL ACTIVITY OF THE ABDOMINAL REGION

CROSS-REFERENCE TO RELATED APPLICATIONS

This application is a U.S. national stage of International Application No. PCT/US2018/030678, filed May 2, 2018, which claims priority to and the benefit of U.S. Provisional Patent Application No. 62/500,771, filed May 3, 2017, each of which is hereby incorporated by reference herein in its entirety.

TECHNICAL FIELD

Provided herein are methods and systems for monitoring acoustical activity from the abdominal region to guide the optimal timing of food ingestion.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The human gastrointestinal (GI) system ingests, digests, absorbs, and propels food throughout its length. The function of the GI system is highly complex and regulated, typically operating in a circadian pattern governed by neurohormonal stimuli. After food is swallowed, it is systematically processed and moved through the stomach, small intestine, and large intestine through a series of tightly coordinated movements. After an ingestion event (i.e. "meal") occurs and food is passed from the stomach to the bowels, the small intestine mixes and propels the food along its length in a process called peristalsis. Peristalsis continues until the food is sufficiently absorbed and residual waste is passed to the small bowel terminus and into the large intestine, or colon, where it is stored until defecation. Between meals, during the fasting period, the bowels are relatively quiescent except for intermittent "housekeeping" waves of peristalsis that sweep through the intestines roughly every 90 minutes. The intestines follow a rhythm that is governed by the amount and frequency of meals: large and/or frequent meals lead to intense and/or continuous intestinal activity; small and/or infrequent meals lead to diminished and/or intermittent intestinal activity.

Intestinal activity is the result of neuromuscular contractions of the inner circular and outer longitudinal muscle layers of the bowel. These contractions, in turn, create sounds and vibrations that can be detected by a listening device. The human ear can often hear the most prominent bowel sounds even without assistance, such as the migrating myoelectric complex (MMC) that sweeps through the bowel during the fasting state, indicating hunger. With assistance from a stethoscope, the human ear can also detect a range of sounds that correlate with intestinal contractions. Some of these sounds fall outside the Hertz range of the human ear, but can be detected by a microphone-enabled listening device.

Continuous monitoring of intestinal activity with a wearable listening device placed on the anterior abdominal wall can allow for noninvasive monitoring of food digestion and passage. Feedback from such a device would be clinically valuable to guide the optimal timing of meals. For example, if a meal ingested earlier in the day were currently undergoing active digestion and peristalsis in the small bowel, then it would be premature to ingest yet another meal; instead, it would be optimal to wait until the current meal is fully digested, absorbed, and passed into the colon, and only then contemplate a subsequent meal. Conversely, if the intestine has been quiescent for a prolonged period, indicating lack of recent digestion, then it would be appropriate to ingest another meal to maintain caloric intake sufficient to meet bodily needs.

Patients with obesity generally consume too many calories, too quickly, and too frequently. Obese individuals often are not aware that they are still digesting a previous meal when initiating yet another meal, leading to a state of overly frequent digestion, mixing, absorption, and propulsion of food. There is little opportunity for inter-prandial housekeeping waves to sweep out poorly digested food, inadequate opportunity to "reset" the neurohormonal homeostatic mechanisms of circadian digestion, and, thus, poor health resulting from excessive calories, dysbiosis of the intestines, and reduced immune function, among other pathogenic mechanisms.

In another context, individuals seeking to enhance physical performance, such as athletes, must time their meals around events in a way that maximizes the availability of calories during exercise, but minimizes bowel activity that can steal vital energy from other body systems required to maintain peak performance. These individuals seek an optimal ingestion window that is close enough to a planned activity to ensure calories are available in sufficient quantity, but far enough from activity to ensure the food bolus has mostly passed into the colon or beyond, thereby minimizing energy-consuming small bowel activity.

There is currently no widely available method for optimizing the timing of food ingestion through noninvasive monitoring of intestinal activity. Thus, there is a need for a method of monitoring acoustical activity of the abdominal region to estimate intestinal activity (e.g. the frequency of digestion events experienced by a user) and guide ingestion behavior in a way that improves health. The result of guidance has potential to reduce weight in people who are obese, to improve performance in athletes seeking to balance energy availability and energy expenditure, or to increase caloric intake in people who are undernourished.

SUMMARY

The following embodiments and aspects thereof are described and illustrated in conjunction with systems, compositions and methods which are meant to be exemplary and illustrative, not limiting in scope.

According to aspects of the present disclosure, a method for optimizing timing of food ingestion by a user is presented. The method comprises receiving, at at least one processor, acoustic data from one or more sensors, each of the one or more sensors being in contact with the user and configured to capture acoustic data from an abdominal region of the user; analyzing, via the at least one processor, the acoustic data to determine a value of one or more digestive metrics; determining an optimal action related to food ingestion based on at least one of the one or digestive metrics; and displaying, via a display device communicatively coupled to the at least one processor, information indicative of the optimal action related to food ingestion.

According to aspects of the present disclosure, a system for optimizing timing of food ingestion by a user is presented. The system comprises a sensor device having a base portion and an acoustic sensor, the acoustic sensor being coupled to the base portion via an extendible member and contacting an abdominal region of the user, the acoustic sensor being configured to capture acoustic data from the abdominal region of the user; a processing device configured to receive the acoustic data from the sensor device via a communications module, the processing device further being configured to analyze the acoustic data to determine a value of one or more digestive metrics; and a display device communicatively coupled to the processing device, the display device being configured to display information indicative of an optimal action related to food ingestion based on at least one of the one or more digestive metrics.

According to aspects of the present disclosure, a method for optimizing the timing of food ingestion by a user is presented. The method comprises measuring acoustic data from the user during a first time period; analyzing the acoustic data to determine (i) a maximum post-meal intestinal rate during the first time period and (ii) a total number of digestions experienced. during the first time period; measuring acoustic data from the user during a second time period; analyzing the acoustic data to determine (i) a running average of an intestinal rate of the user during the second time period and (ii) a current number of digestions experienced during the second time period; and providing information indicative of an optimal action related to food ingestion during the second time period based on (i) a ratio of (a) the running average of an intestinal rate of the user during the second time period to (b) the maximum post-meal intestinal rate during the first time period, and (ii) a ratio of (a) the current number of digestions experienced during the second time period to (b) the total number of digestions experienced during the first time period.

These and other capabilities of the invention, along with the invention itself, will be more fully understood after a review of the following figures, detailed description, and claims.

BRIEF DESCRIPTION OF THE DRAWINGS

Exemplary embodiments are illustrated in referenced figures. It is intended that the embodiments and figures disclosed herein are to be considered illustrative rather than restrictive.

Figure 1:
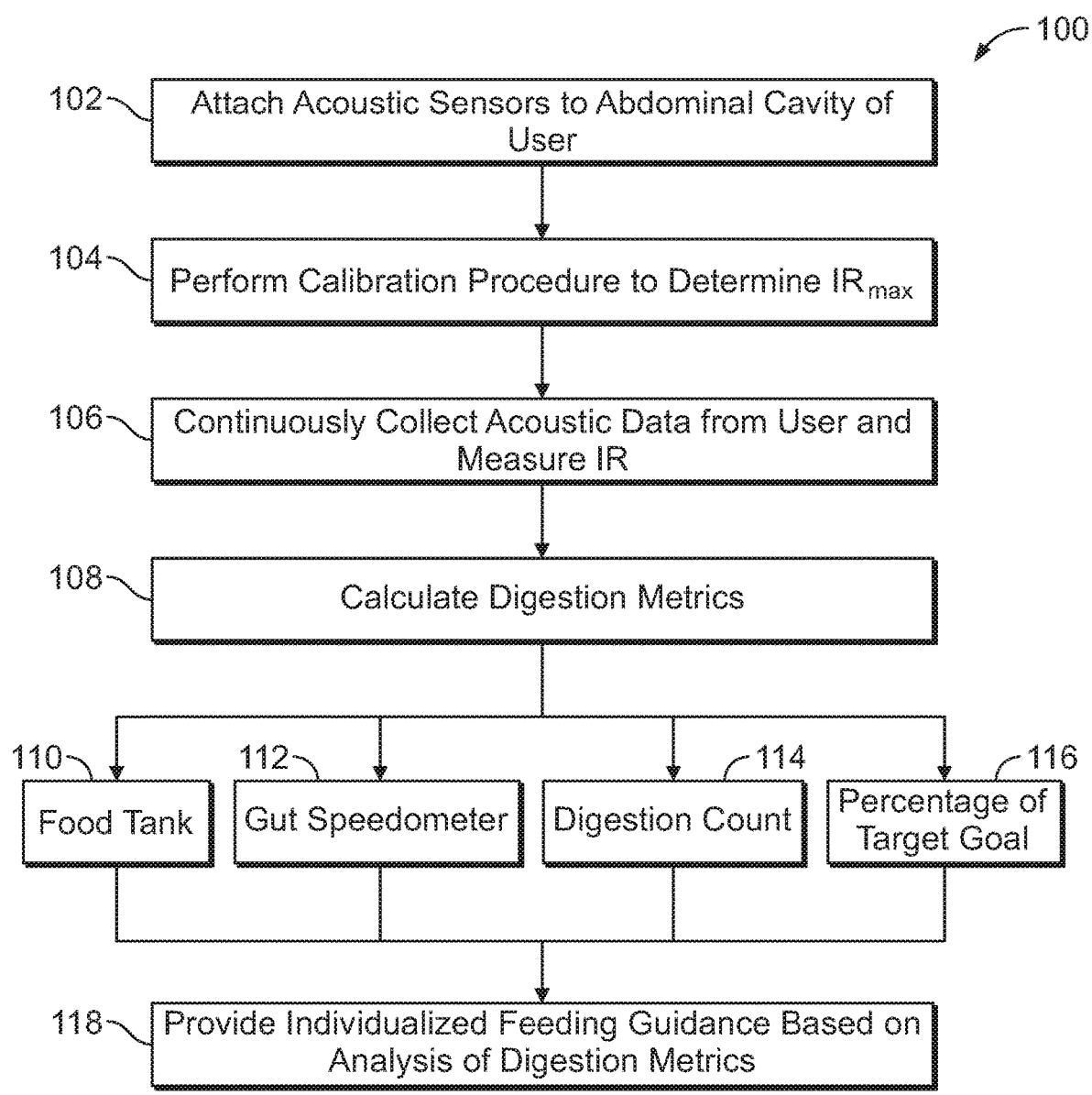
FIG. 1 depicts an implementation of a process flow for optimizing the timing of food ingestion, according to aspects of the present disclosure herein.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

All references cited herein are incorporated by reference in their entirety as though fully set forth herein. Unless defined otherwise, technical and scientific terms used herein have the same meaning as commonly understood by one of ordinary skill in the art to which this disclosure belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims.

As noted above, there is need for a method of optimizing the timing of food ingestion through noninvasive monitoring of intestinal activity. A method to optimize meals according to physiologic patterns of the intestinal system would have major implications for human health; it would allow for evidence-based management of obesity and for optimizing the timing of nutrition to align with the natural rhythms and cycles of digestion. Monitoring acoustical activity of the abdominal region can estimate intestinal activity and has potential to guide ingestion behavior in a way that improves health. The methods described herein may allow contextually appropriate feeding guidance that promotes appropriate weight reduction in people who are obese, improve performance in athletes seeking to balance energy availability and energy expenditure, or increase caloric ingestion in people who are undernourished.

Therefore, disclosed herein are methods that evaluate dynamic changes in acoustic intestinal rate (IR), defined as the number of digestion events per minute, to provide guidance about optimizing the timing of food ingestion. A digestion event is a contraction or similar event in the digestive system that produces a distinctive acoustic signature. Using digestion metrics derived from the intestinal rate measurements, the method presents guidance to users about whether and when to eat in a manner that is physiologically appropriate and promotes health.

The method may be applied using one or more biosensor(s) to measure abdominal sounds and communicate the acoustic data to a processor for further analysis and reporting. According to some embodiments, one or more biosensors may be employed to collect acoustic information from the user for evaluation. The acoustic information may then be measured to generate IR data, which can be further analyzed according to the methods herein. The acoustic data generally includes an acoustic intensity measured over a certain time period. In one example, a single digestion event may be evidenced by a rapid rise and fall in the acoustic intensity, followed by a short oscillation of the acoustic intensity. Other acoustic signatures are also possible that can be determined to count as a digestion event.

The method uses IR data prospectively to identify changes in intestinal activity over time, and then uses the results to provide evidence-based guidance about feeding. For example, if an individual is contemplating whether or not to eat, the result of IR analysis may indicate that a previous meal is still being actively digested, suggesting that it is premature to consume yet another meal. In some implementations, if an average IR over the previous 20 minutes of acoustic recording indicates sustained high intestinal activity, then it is not physiologically appropriate to eat.

Figure 2:
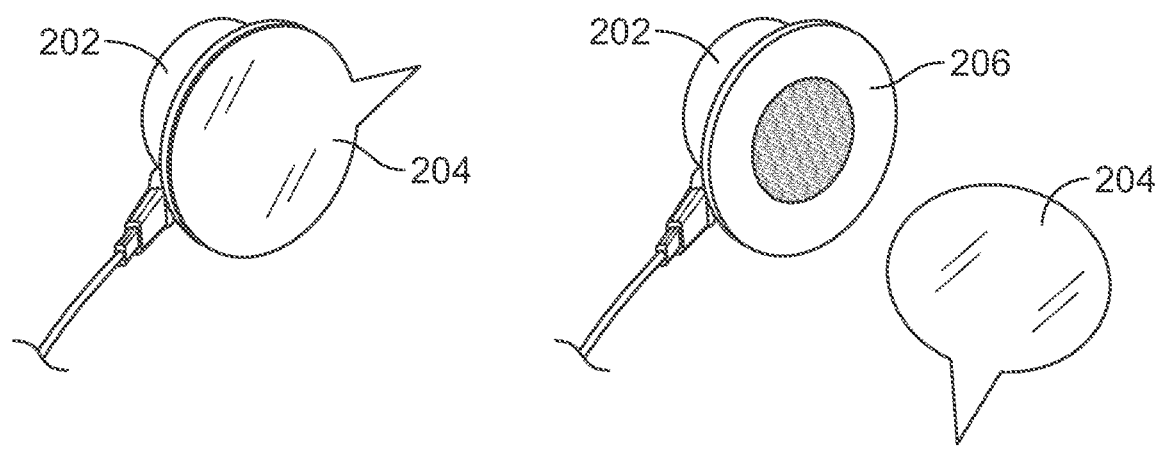
FIG. 2 depicts a sensor to monitor acoustic data from a user, according to aspects of the present disclosure herein.

Turning to FIG. 1, a method 100 for monitoring intestinal activity and optimizing timing of food ingestion is shown. At step 102, one or more sensors are placed on the user's abdominal region, to monitor acoustic data from the abdominal region. The sensors include one or more standard microelectric microphones that adhere to the abdominal wall, and collect and transmit acoustic data to a processor via a communications module for further analysis. According to some embodiments, the sensors may be of the type disclosed in WO2014/039404 A1 "Multisensor Wireless Abdominal Monitoring Apparatus, Systems, and Methods," or as shown in FIG. 2 FIG. 2 illustrates an acoustic sensor 202 having a protective film 204 disposed thereon, and show the acoustic sensor 202 with the protective film 204 detached, thereby exposing a facing portion 206 that is configured to contact the user's abdominal region. According to other embodiments, a wireless sensing device could fit into the user's umbilicus (i.e. navel) in order to maintain a low profile, or may be placed within a form-fitting abdominal belt. Other embodiments are also contemplated that are unobtrusive and offer a low profile. One such wireless sensing device that may be adapted is the smart stethoscope, a Bluetooth® enabled electronic sensor attached to a stethoscope for monitoring heart sounds, available at www.ekodevices.com.

Figure 3:
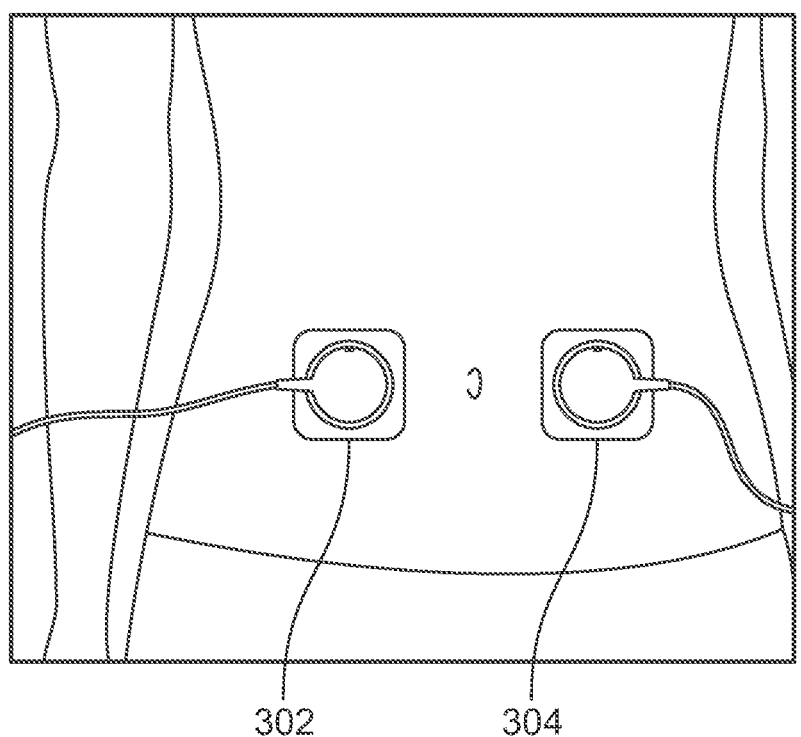
FIG. 3 depicts multiple of the sensors of FIG. 2 being applied to the abdominal region of a user, according to aspects of the present disclosure herein.

In a further embodiment, a sensor could be clipped onto or otherwise coupled to the user's belt or the top of the user's pants. In yet a further embodiment, a sensor could be coupled to the user's undergarments and face inwardly to make contact with the user's skin. For example, a sensor could clip onto the waistband of the user's underwear. In another embodiment, a sensor device can include a base portion that couples to the user or an article of clothing of the user and an acoustic sensor (such as a microphone) coupled to the base portion via an extendible member or similar mechanism. The base portion can be coupled to the user at any location, and the extendible member can extend the acoustic sensor to the desired location on the user. For example, the ideal location on the user at which to measure acoustic data from the user's intestines may be located far away from a suitable attachment point on the user's clothing. Tape, glue, adhesive, or some other external attachment mechanism could be used to attach the sensor to the user's skin at that location, but that can be undesirable for the user. Thus, the base portion can be securely coupled to the user's clothing where convenient, and the acoustic sensor can extend to appropriate location on the user where acoustic data is measured. In at least one embodiment, the base portion is securely coupled to the user's belt, pants, or undergarment, and the extendible member extends upward such that the acoustic sensor contacts the user's skin near the user's navel. The extendible member can extend telescopically or can extend by unfolding. Other configurations of the extendible member are also contemplated. Generally, the extendible member possesses some degree of flexibility to allow for movement, but is rigid enough such that contact between the acoustic sensor and the user's skin is maintained due to the rigidity of the rod and without the use of any other external attachment mechanism, such as tape, adhesive, or the like. The sensor device generally also has a communications module configured to transmit the captured acoustic Illustrated in FIG. 3 are two sensors 302 and 304 attached to a user. Although only the two sensors 302 and 304 are shown in FIG. 3, alternative sensor arrangements may be used. According to some embodiments, a single sensor is sufficient if placed within 2-4 cm of the user's umbilicus. According to other embodiments, having two or more sensors may allow for more precise identification of a signal location within a user. When using more than one sensor, logic is needed to detect the case where the same auditory signal captured by a plurality of sensors, and correct for this condition so that the signal is only considered once and "double counting" is avoided.

At step 104, the one or more sensors are used to perform a calibration procedure to set the boundaries of an IR profile for a user. Each user has an individual IR profile that defines when the user is experiencing low, medium, or high intestinal activity. To perform the calibration procedure, the user consumes a standardized meal containing a fixed volume and calorie content. Example calibrated meals are listed below, all having similar estimates of volume and calorie content: (1) Corner Bakery Cafe® full turkey and swiss sandwich, bag of potato chips, chocolate chip cookie, and a 12 oz can of soda or juice; (2) McDonald's® double quarter pounder hamburger with cheese, medium french fries, and a medium soda; or (3) Panda Express® eggplant Tofu bowl, side of fried rice, and a medium soda.

Figure 4:
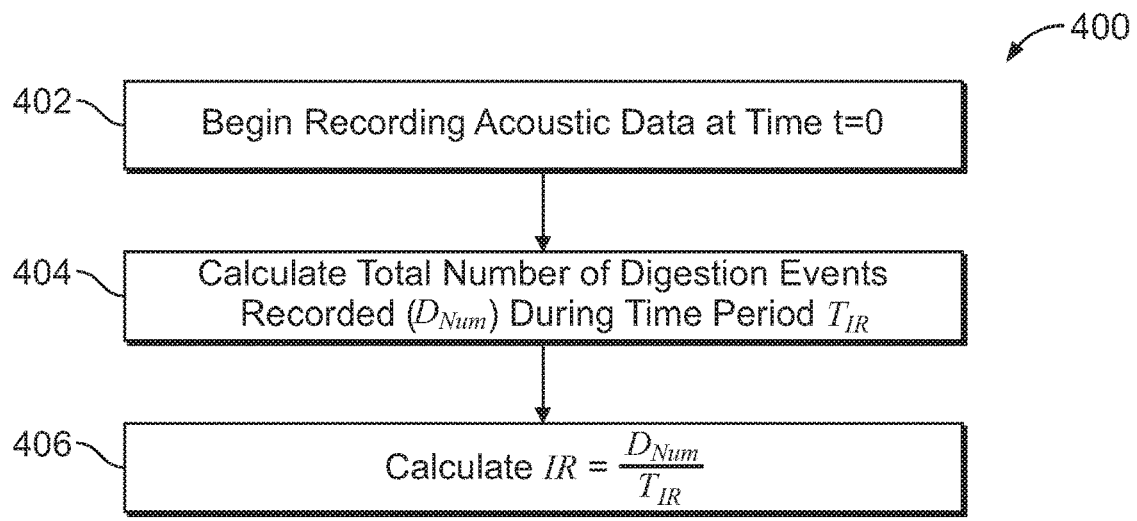
FIG. 4 depicts an implementation of a process flow for obtaining an intestinal rate measurement of a user, according to aspects of the present disclosure herein.

The user consumes the test meal over a maximum of 30 minutes. The one or more sensors are used to capture acoustic data from the user. This acoustic data is then used to determine the user's IR over any given time period. IR data comprises one or more IR measurements. The process of determining of obtaining a single IR measurement is illustrated in FIG. 4, where an exemplary method 400 of obtaining an IR measurement is shown. At step 402, corresponding to time t=0, the sensors placed on the user begin recording acoustic data and counting the number of digestion events the user experiences. The sensors count the number of digestion events for a time period Ta, which is measured in minutes. At step 404, corresponding to time $t=T_{IR}$, the recorded digestion events are summed to obtain the total number of digestion events experienced, denoted as $D_{Num}$. At step 406, the individual IR measurement is obtained by dividing $D_{Num}$ by $T_{IR}$.

An individual IR measurement is thus obtained by recording the number of digestion events that occur in a certain time period and dividing that number by the number of minutes in the time period. For example, if twenty digestion events are detected ($D_{Num}=20$) over a time period of 10 minutes ($T_{IR}=10$), the single IR measurement would be equal to two digestion events per minute. In an exemplary embodiment, time period $T_{IR}$ is any one of 1 minute, 2 minutes, 5 minutes, 10 minutes, 30 minutes, 60 minutes (1 hour), 360 minutes (6 hours), 720 minutes (12 hours), or 1,440 minutes (24 hours). Other time periods are also contemplated.

A mean IR value for an individual time period, denoted as $IR_{Mean}$, may also be calculated by taking the sum of the individual IR measurements for the time period and dividing by the number of IR measurements obtained for that time period. For example, if a total of N IR measurements are recorded in a time period t and the nth IR measurement in the time period t is denoted as $IR_n$, the mean IR value for the time period may be calculated thusly:

$$IR_{Mean} = \frac{\sum_{n=1}^{N} IR_n}{N}.$$

Figure 5:
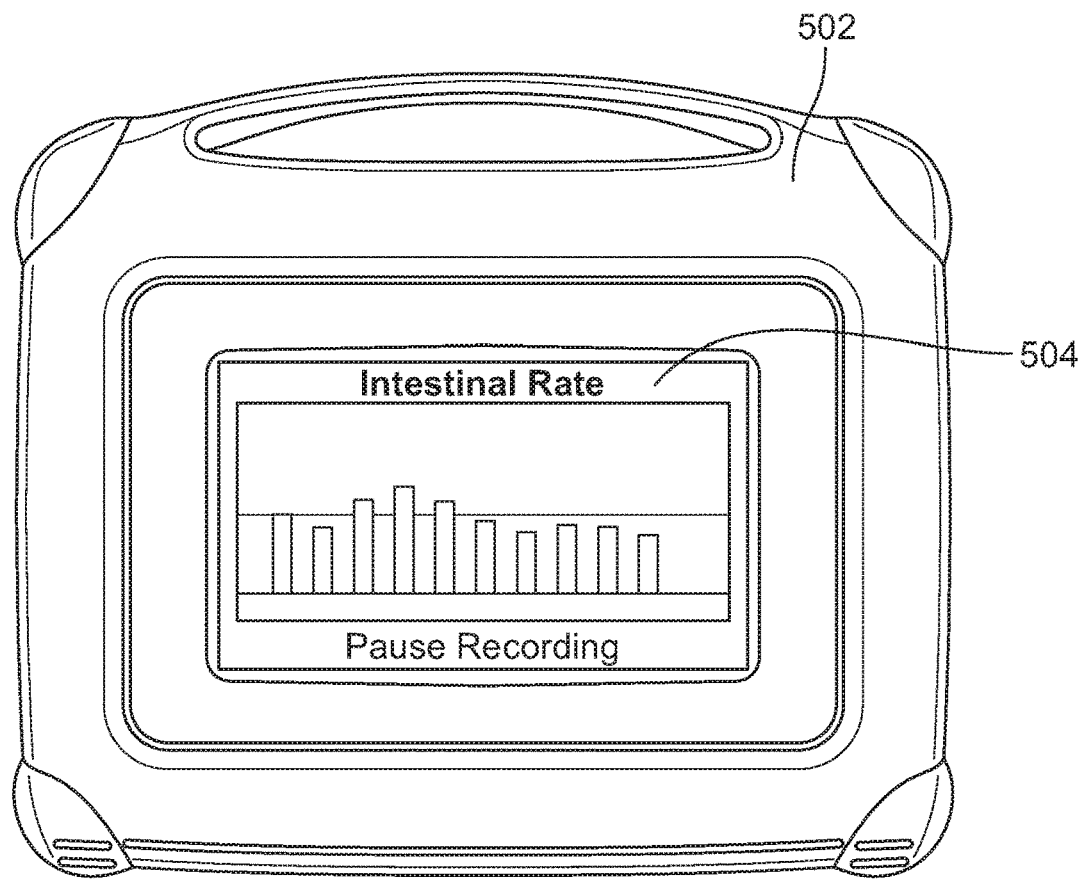
FIG. 5 depicts a portable processing device for measuring and displaying intestinal rate data, according to aspects of the present disclosure herein.

According to some embodiments, the acoustic data collected by the one or more sensors is communicated to a processor, such as a bedside computer configured to analyze the acoustic data. The processor may receive the acoustic data from the one or more sensors via a wired connection. Alternatively, the one or more sensors may be configured to wirelessly transmit data to the processor, such as by Wi-Fi, Bluetooth®, or other wireless capability. The processor may be in the form of a desktop computer, laptop computer, medical appliance, tablet, smart phone, or other processing device capable of receiving real-time acoustic data from the sensor(s), measuring IR, and performing further analysis as detailed below. FIG. 5 illustrates one example of a portable processing device 502 for measuring and reporting IR, and capable of adaptation (for example, via additional software instructions or programming) to perform the IR analysis and reporting as disclosed herein. As shown portable processing device 502 has a display 504 that may display relevant information.

According to other embodiments, the processor is remotely located from the one or more sensors, but communicatively coupled to the sensors via a data network. Thus, the processor may be located at a centralized location, such as a monitoring station or nurses' station. In some embodiments, the data network is the Internet, local area network, or a private intranet. Additionally, the data may be encrypted or otherwise secured during transmission.

Following the user's calibration meal, IR data is measured continuously for eight hours as the meal passes through the stomach, small bowel, and into the colon. A maximum IR value recorded during the eight-hour period, denoted as $IR_{Max}$, is benchmarked as the "high intestinal activity" value for the user. This maximum IR can subsequent used to calculate a variety of metrics that can help the user analyze when an appropriate time to ingest additional occurs.

At step 106 of method 100, the one or more sensors continuously collect acoustic data from the user and perform individual IR measurements. At step 108, the acoustic data and the IR measurements are used to determine the value of one or more digestion metrics that can assist in optimizing the timing of food ingestion.

Figure 6A:
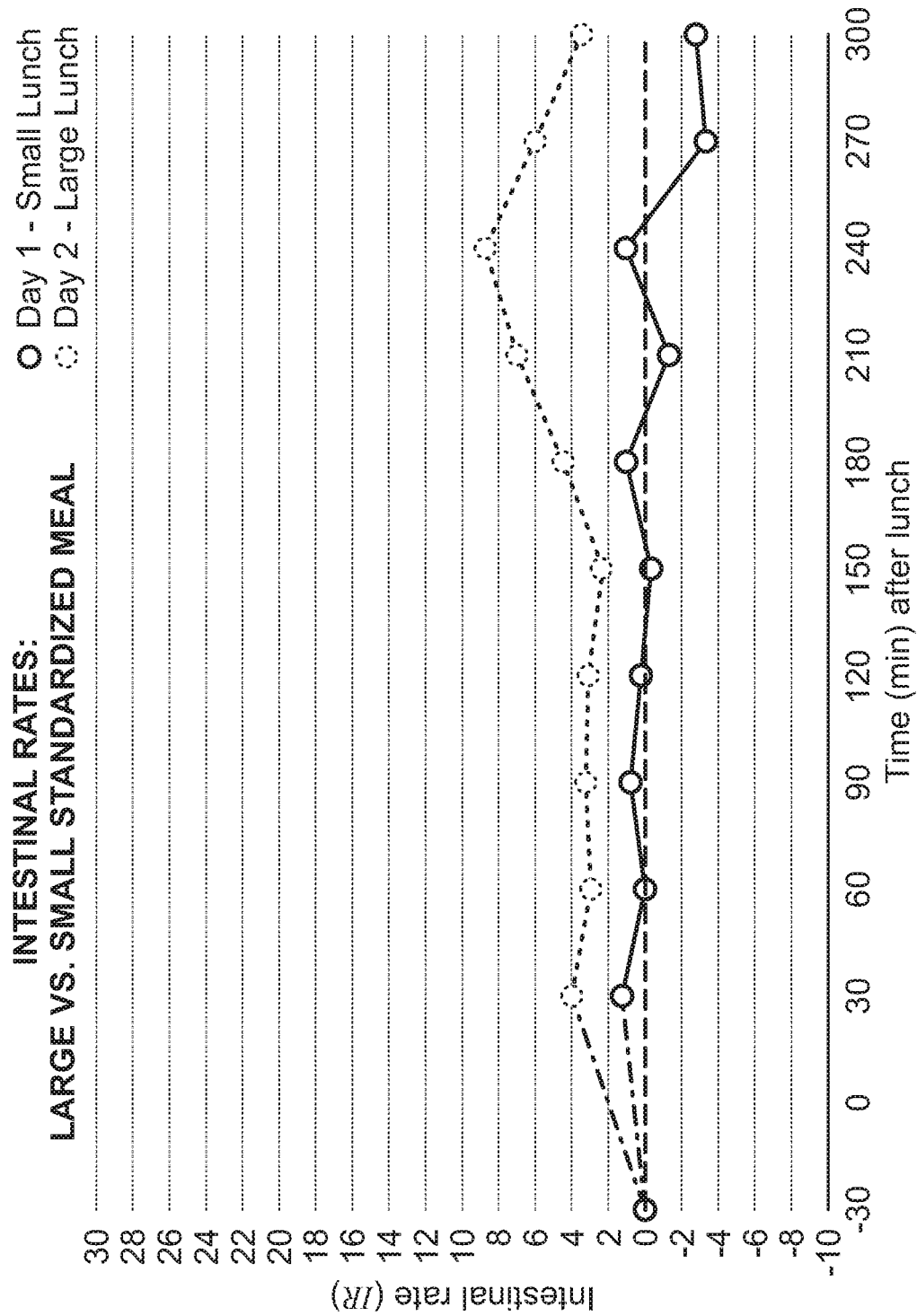
FIG. 6A depicts an example plot of the median difference between measured IR and baseline IR following a large meal and a small meal, according to aspects of the present disclosure herein.
Figure 6B:
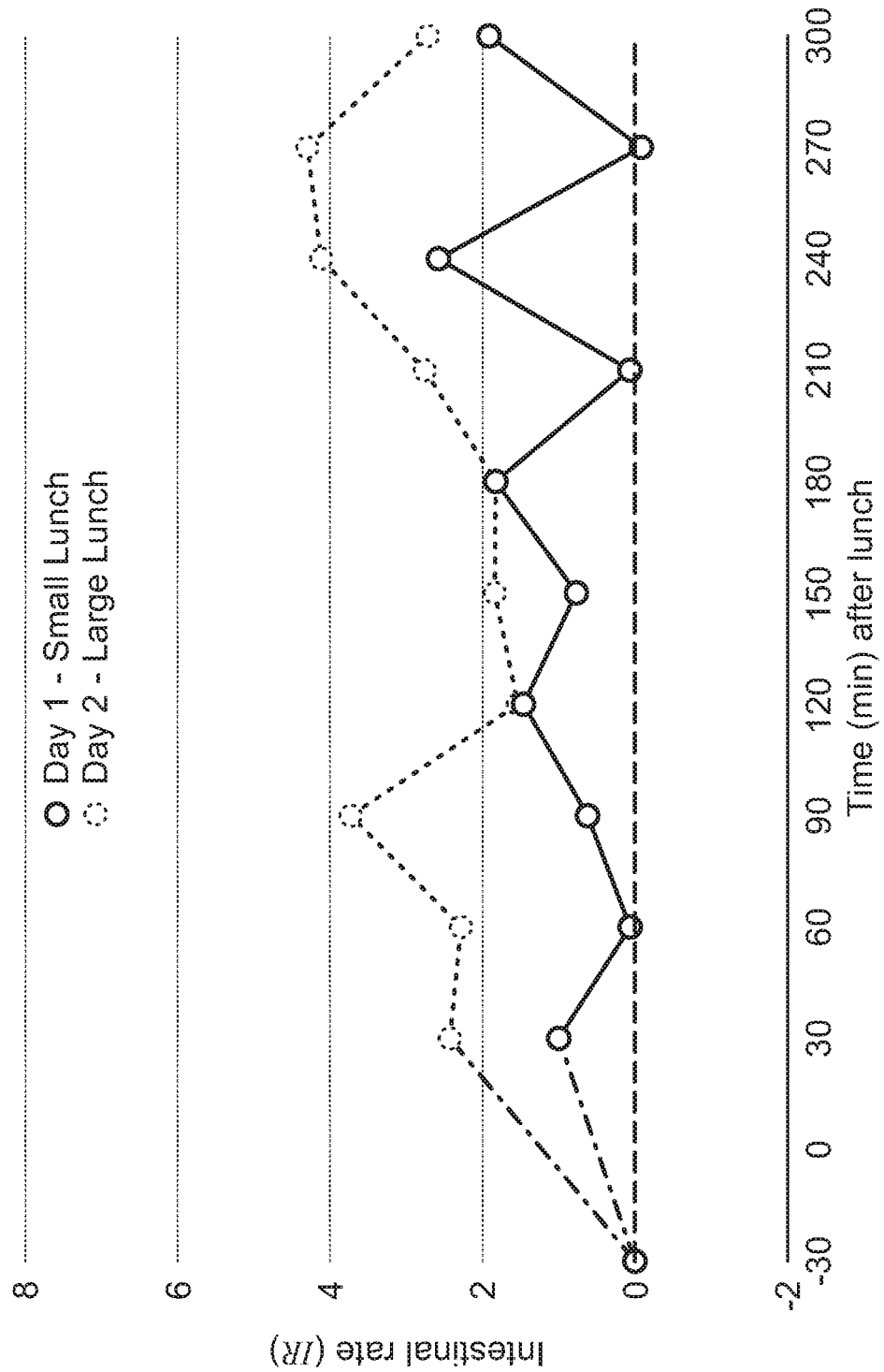
FIG. 6B depicts another example plot of the median difference between measured IR and baseline IR following a large meal and a small meal, according to aspects of the present disclosure herein.

In an example, a number of users of varying age and body mass index wore acoustic sensors. IR measurements were obtained for the users over at least two sequential days. Each user's pre-meal baseline intestinal rate was also determined. On the first day, each user consumed a small standardized lunch having a known number of calories. On the second day, each user consumed a large standardized lunch having a known number of calories. Each user's intestinal rate was measured for a period of ten minutes, every thirty minutes, and compared against the user's predetermined pre-meal baseline intestinal rate. The median difference between the measured IR and the baseline IR for both the small meal and the large meal for all users was plotted as a function of the number of minutes after the meal. These plots for two different studies are illustrated in FIG. 6A and FIG. 6B. As is shown, the measured IR differences over the course of the day generally varied from about 0 per minute, to a maximum of about 4-8 per minute. The largest difference between the recorded IR and the baseline IR occurred between about 210 minutes following a meal and about 270 minutes following a meal. Importantly, the difference between the recorded IR and the baseline IR during this period is greater for large meals than it is for small meals. These examples illustrate that the IR measurements tend to undergo sustained increases following large meals, and that by monitoring a patient's bowels for acoustic evidence of digestive events, one can determine the volume of food consumed by the patient. The principles described herein can thus provide effective and accurate benchmarks and metrics on which to base guided monitoring.

Referring now to step 110, a food tank metric can be calculated. The food tank metric comprises a running average of the user's intestinal rate. The food tank metric is a measure of how "full" the intestines are based on a running average of the immediate previous 20 minutes of intestinal activity, which is expressed as a percentage of $IR_{Max}$. $IR_{Max}$ for each individual user is based on the calibration procedure performed in step 104. Because momentary IR can vary from minute-to-minute, the food tank metric samples IR measurements over a 20-minute period and calculates a moving average, denoted as $IR_{20MinMean}$. For example, in an exemplary embodiment where IR measurements are taken by counting the number of digestion events in one minute, the moving average of the food tank metrics will update every minute, and will be the average of the previous 20 IR measurements. This 20-minute moving IR average is divided by the user's $IR_{Max}$ and multiplied by 100 to produce the final value of the food tank metric:

$$\text{Food Tank Metric} = \frac{IR_{20MinMean}}{IR_{Max}} \times 100.$$

Here, $IR_{20MinMean}$ is the value of $IR_{Mean}$ when the time period $t=20$ minutes. Thus, subsequent IR measurements following the calibration procedure can be expressed as a percentage of the user's $IR_{Max}$ using the food tank metric.

This food tank metric can be presented to the user as a "fuel gage" and can be divided into red, yellow, and green zones. For example, if after a standardized calibration meal a user achieves an $IR_{Max}$ of 48, then 48 becomes "100% full" on the food tank metric for that individual user. An IR of 0 is the bottom of the food tank, or "0% full." A value of IR=20 would be 20/48=41.6% "full" on the food tank metric. A subsequent 20-minute period with a running average of 30 would yield a food tank value of 30/48=62.5% full.

Generally, a value for the food tank metric greater than or equal to a first predetermined percentage of the user's $IR_{Max}$ is in the "Red Zone," which indicates to the user that they are full and should not eat any more food. The first predetermined percentage can be about 60%, about 61%, about 62%, about 63%, about 64%, about 65%, about 66%, about 66.6%, between about 60% and about 70%, between about 60% and about 65%, or between about 65% and about 70%. A food tank metric value less than the first predetermined percentage of the user's $IR_{Max}$ but greater than a second predetermined percentage of the user's $IR_{Max}$ is in the "Yellow Zone," which indicates a medium level of fullness and that the user should likely food ingestion for the time being. The second predetermined percentage can be about 30%, about 31%, about 32%, about 33%, about 33.3%, between about 30% and about 40%, between about 35% and about 40%, or between about 30% and about 35%. A food tank metric value that is less than the second predetermined percentage of the user's $IR_{Max}$ is in the "Green Zone," and indicates to the user that their stomach is essentially empty and that they are approved to ingest food if they are hungry: ("Empty—Okay to Eat if Hungry"). The food tank measurements can be tracked over time to demonstrate trends over the course of a day or longer.

At step 112 of method 100, a gut speedometer metric can be calculated, which is a measure of how quickly the intestines are moving at any moment in time. Unlike the food tank metric, which reflects a running IR average over the previous immediate 20 minutes of continuous use, the gut speedometer metric provides an up-to-date "snapshot" of current IR, defined by the IR over the past two minutes. The gut speedometer metric is denoted as $IR_{Current}$, and is calculated by dividing the number of digestion events detected during the previous two minutes. For example, if 10 digestion events are detected ($D_{Num}$=10) over the previous two minutes ($T_{IR}$=2), then the gut speedometer metric would be equal to 5 digestion events per minute. Thus, the gut speedometer metric comprises a measure of the current intestinal rate.

At step 114 of method 100, a daily digestion count metric is calculated. The daily digestion count metric is a measure of the total number of "digestions" during a time period, which is generally a single day. The count starts at midnight and continues up until the current time, and is updated in real time. Each intestinal acoustic signal detected by the one or more sensors is counted as a "digestion," and the cumulative total since midnight, $D_{Total}$, is calculated.

At step 116 of method 100, a percentage of target goal metric is calculated. This metric is a measure of the percentage of a targeted number of daily digestions achieved up until the current time. For example, if a user targets a maximum of 15,000 total digestions over the course of a day, but has already achieved 20,000 total digestions, then the percentage of target goal metric would read "133% of target goal." Because the IR of a user is proportional to the amount of food digestion and passage through the intestines (i.e. more food=higher IR; less food=lower IR), there is a benefit to setting a targeted daily digestion count to guide food ingestion. For example, an individual seeking to lose weight might target a $D_{Total}$ of 14,400 or less, corresponding with a daily $IR_{Mean}$=10 digestions per minute. Using this goal as a target, an individual can monitor progress towards that goal over the course of a day.

The percentage of target goal is calculated as the percent ratio of the daily digestion count metric to a targeted daily digestion count (denoted as $D_{Goal}$):

$$\text{Percentage of Target Goal} = \frac{D_{Total}}{D_{Goal}} \times 100.$$

For example, if at LOAM a user has accumulated 2000 digestions, and if that user has set a target of 12,000 digestions for the day, then the system would indicate 2000/12,000*100=16.6% of target goal. This value provides real-time, continuous guidance to the user about whether food ingestion is above goal, below goal, or on goal as the day progresses. The target daily digestion count can be based on a total number of digestions experienced by the user during the calibration procedure. For example, an overweight user may experience an average of 20,000 daily digestions. The target daily digestion count may be to reduce the daily digestion count by a predetermined number of digestions (e.g. 500 digestions for a daily digestion count of 19,500), or to reduce the daily digestion count by a predetermined percentage of the average daily digestion count (e.g. 5% for a daily digestion count of 19,000). Similarly, an underweight user may have a target daily digestion count that is a predetermined number of digestions higher than their average daily digestion count, or a predetermined percentage of their average daily digestion count.

Figure 7:
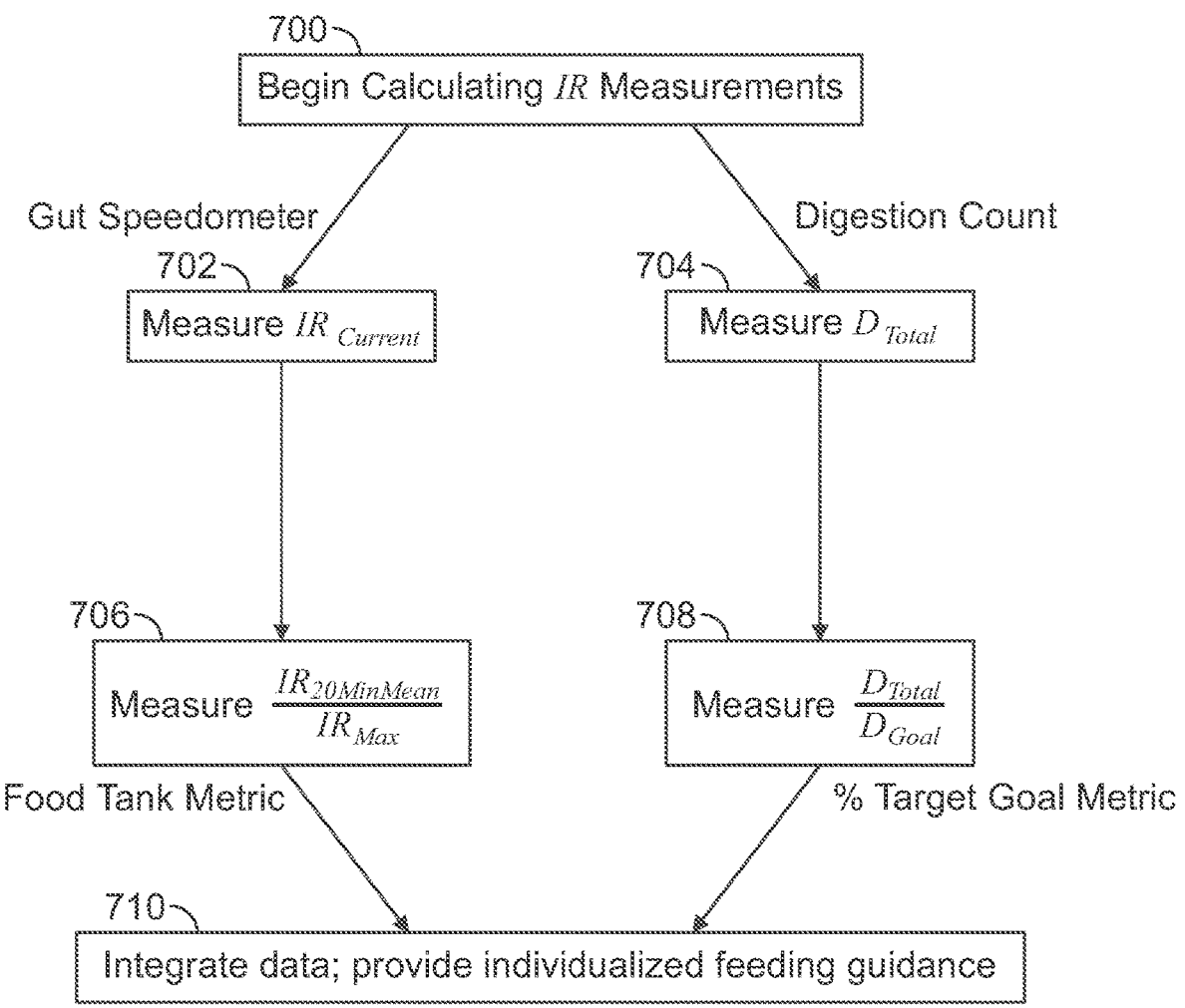
FIG. 7 depicts the relationship between various digestion metrics, according to aspects of the present disclosure herein.

The relation between the various metrics is illustrated in FIG. 7. As shown, the system begins recording acoustic data and calculating IR measurements 700. As the IR measurements are being calculated, the gut speedometer metric 702 and the digestion count metric 704 are determined. As discussed herein, the gut speedometer metric 702 is denoted as $IR_{Current}$ and is an average IR for a user for the past two minutes. The digestion count metric 704 is denoted as $D_{Total}$ and is the total number of digestion events the user has experienced in the current day or 24-hour period. The food tank metric 706, which is the running average of the immediate previous 20 minutes of intestinal activity, can be calculated in some implementations by using $IR_{current}$ to determine $IR_{20MinMean}$ (for example, by adding together the ten previous $IR_{Current}$ measurements), and dividing $IR_{20MinMean}$ by the user's $IR_{Max}$. In other implementations, $IR_{20MinMean}$ is determined as the running average of the previous 20 IR measurements, as discussed herein. The percent of target goal metric 708 can be calculated by dividing $D_{Total}$ by $D_{Goal}$. Once those metrics are known, data can be integrated and individualized feeding guidance 710 can be given to the user.

At step 118 of method 100, individualized feeding guidance can be provided to the user. This individualized feeding guidance can be displayed to the user via a display device that is communicatively coupled to the processing device. As discussed above, the food tank metric can generally be divided into three zones: red, yellow, and green. For purposes of providing feeding guidance to the user, the percentage of target goal metric can be divided into five separate categories: >100%, 90-99%, 80-89%, 50-79%, and <50%. Combining the three zones for the food tank metrics and the five categories for the percentage of target goal metric gives fifteen different possible combinations upon which the individualized feeding guidance can be based. The feeding guidance indicates to the user an optimal action related to food ingestion, and is thus generally based on (i) the running average of the intestinal rate (i.e. the food tank metric) and (ii) the ratio of the total number of digestive events experienced during the time period to a goal number of digestive events for the time period (i.e. the percentage of target goal metric). This guidance is shown in Table 1 below. Each combination of the two metrics results in a different message being sent to the user. Each message summarizes the current value of the food tank metrics and the percentage of target goal metric, and provides the user with advice on how to proceed. For example, a food tank metric value in the red zone combined with a percentage of target goal metric >100% means that the user is currently digesting food, and has already exceed their target number of digestions for the day. The message to the user can thus be: "You're in the red zone now and over your daily target. You might need to lay off the food." In one embodiment, fourteen other possible messages to the user are contemplated as detailed in Table 1.

TABLE 1

| Food Tank Measurement | % Target Goal Metric | Sample Insight Message |
|---|---|---|
| Red Zone | >100% | You're in the red zone now and over your daily target. You might need to lay off the food. |
| Red Zone | 90-99% | You're in the red zone now and nearly at your daily target. You might need to lay off the food. |
| Red Zone | 80-89% | You're in the red zone now and getting close to your daily target. Hold off on eating until you get out of the red zone, then eat sensibly to avoid overshooting the target. |
| Red Zone | 50-79% | You're in the red zone now but on target for the day. Hold off on eating until you get out of the red zone, then eat sensibly when you're hungry again. |
| Red Zone | <50% | You're in the red zone now but under target for the day. Hold off on eating until you get out of the red zone, but then you can start eating again when you're hungry. |
| Yellow Zone | >100% | You're in the yellow zone now and over your daily target. You might need to lay off the food. |
| Yellow Zone | 90-99% | You're in the yellow zone now and nearly at your daily target. You might need to lay off the food for a bit. |
| Yellow Zone | 80-89% | You're in the yellow zone now and getting close to your daily target. Hold off on eating until you get into the green zone, then eat sensibly to avoid overshooting the target. |
| Yellow Zone | 50-79% | You're in the yellow zone and on target for the day. You should eat sensibly when you're hungry again. |
| Yellow Zone | <50% | You're in the yellow zone now but under target for the day. You should eat sensibly when you're hungry again. |
| Green Zone | >100% | You're in the green zone now but over your daily target. Take it easy on the food because you've already overshot. |
| Green Zone | 90-99% | You're in the green zone now but nearly at your daily target. You can eat if you're hungry, but be sensible because you're about to overshoot your daily goal. |
| Green Zone | 80-89% | You're in the green zone now but getting close to your daily target. You can eat if you're hungry, but try not to overdo it. |
| Green Zone | 50-79% | You're in the green zone now and on target for the day. Go ahead and eat sensibly if you get hungry again. |
| Green Zone | <50% | You're in the green zone and on target for the day. Go ahead and eat a bit (sensibly, of course!) |

The feeding guidance to the user can also be based only on the Food Tank metric or only on the percentage of target goal metric. For example, a user with a food tank metric value in the green zone might be told that it is ok to eat. A user with a food tank metric value in the yellow zone might be told to watch what the user is eating and that the user may want to think about stopping eating or not starting eating. A user with a food tank metric value in the red zone may be told to specifically to stop eating or to not start eating. Other guidance messages are also contemplated.

Similarly, a user with a percentage of target goal metric above 100% may be told to stop eating or to not eat any more. A user with a percentage of target goal metric between 90-99% may be told that they are almost near their goal and that they should not eat much more. A user with a percentage of target goal metric between 80-99% may be told that they have a little bit of room before they hit their goal and that they can eat a little bit more. A user with a percentage of target goal metric between 50-79% may be told that they are not that close to their target goal and to go ahead and eat what they want without worrying. A user with a percentage of target goal metric less than 50% may be told that they are far away from their target goal and they specifically need to eat in order to catch up. Other guidance messages are also contemplated.

Figure 8A:
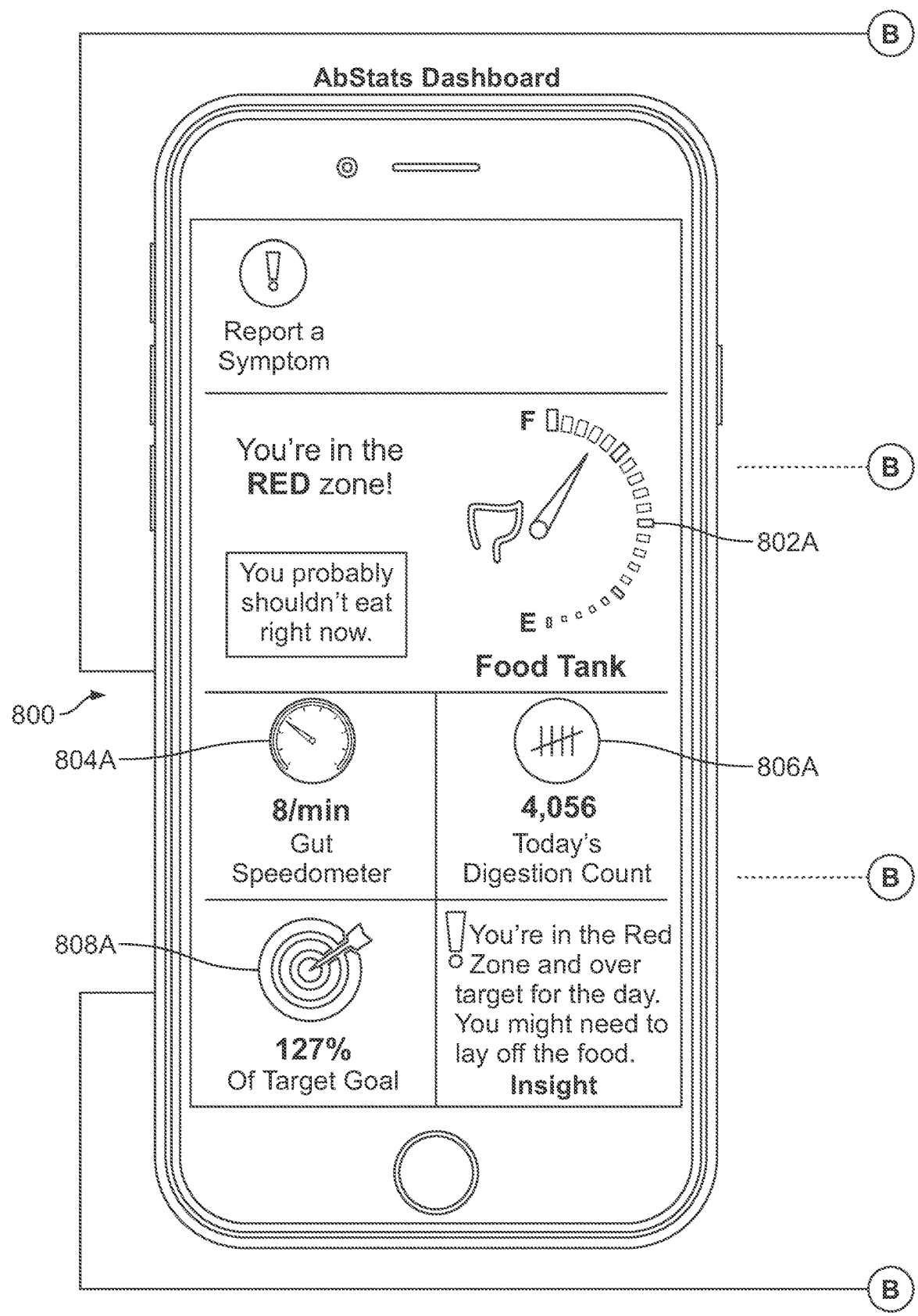
FIG. 8A depicts a first view of a user dashboard for viewing the calculated metrics, according to aspects of the present disclosure herein.
Figure 8B:
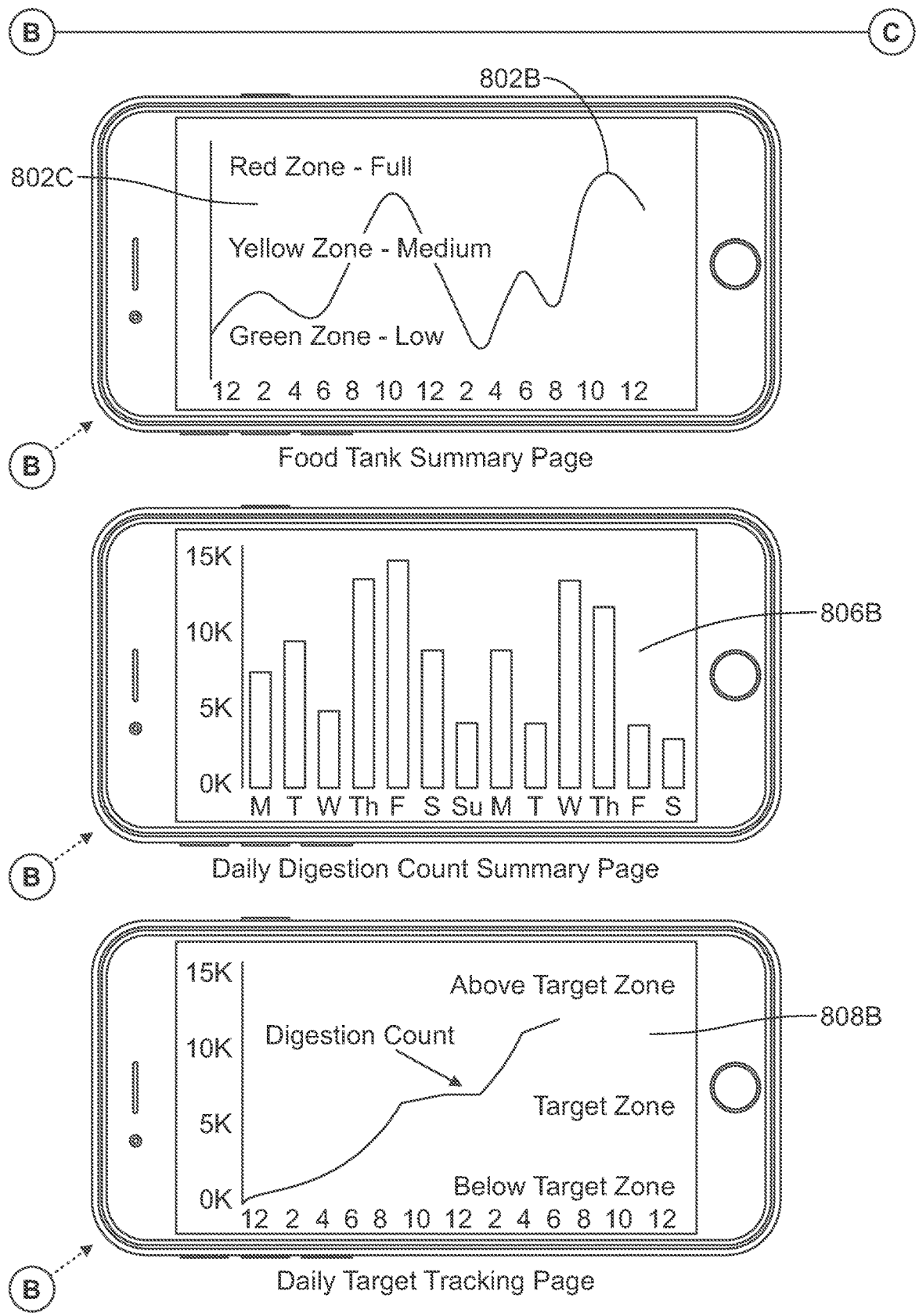
FIG. 8B depicts a second view of a user dashboard for viewing the calculated metrics, according to aspects of the present disclosure herein.
Figure 8C:
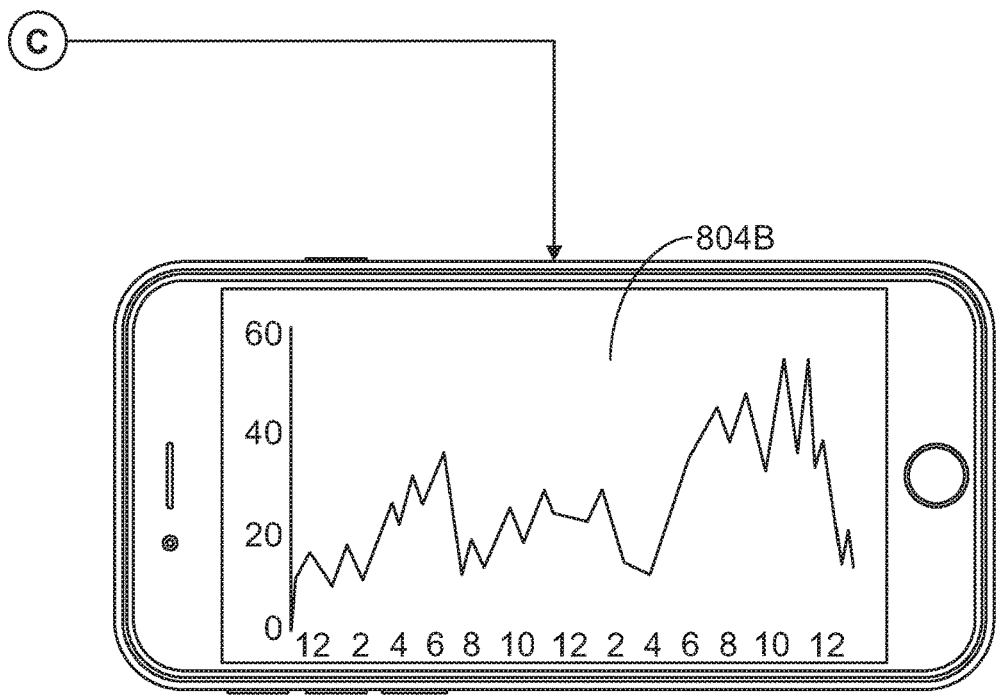
FIG. 8C depicts a third view of a user dashboard for viewing the calculated metrics, according to aspects of the present disclosure herein.

Referring now to FIGS. 8A-8C, a user dashboard 800 is illustrated. The user dashboard 800 provides information on the various calculated metrics to the user. A food tank gauge 802A (FIG. 8A) and a food tank summary chart 802B (FIG. 8B) provide information on the calculated food tank metric. The food tank gauge 802A represents the calculated value of the food tank metric as a visual gauge that is continually updated during usage. This food tank gauge 802A provides the user with a concise summary of the calculated value of the food tank metric, which is the 20-minute rolling average of the IR measurements as a percentage of the user's $IR_{Max}$. The food tank summary chart 802B charts the calculated value of the food tank metric throughout the day, and shows the red, yellow, and green zones for the user. The food tank summary chart 802B thus provides the user with an easy to read indication of what zone their food tank metric is in. The food tank summary chart 802B can demonstrate trends in the food tank metric over a single day, or over longer or shorter time periods. The user dashboard 800 also includes a food tank zone indicator 802C (FIG. 8B) which indicates to the user which zone the current food tank metric resides in. Food tank zone indicator 802C may multiple horizontal regions corresponding to different zones, e.g. green zone, yellow zone, and red zone. These horizontal regions can be separated by lines or borders, or can be differentiated by some other characteristic, such as color or background pattern/design. User dashboard 800 can also indicate to the user which zone the current food tank metric resides in via a color system. A food tank metric value in the red zone can be indicated with a red light or red text. A food tank metric value in the yellow zone can be indicated with a yellow light or yellow text. A food tank metric value in the green zone can be indicated with a green light or green text.

The user dashboard 800 further includes a gut speedometer gauge 804A (FIG. 8A) that provides the user with an indicator of the current value of the gut speedometer metric, and a gut speedometer summary chart 804B (FIG. 8C) which shows trends in the gut speedometer metric over certain time periods.

The user dashboard 800 also includes a daily digestion count indicator 806A (FIG. 8A) and a daily digestion count summary chart 806B (FIG. 8B). The daily digestion count indicator 806A provides the user with the current value of the cumulative number of digestions for the day. The user is thus able to quickly glance at their phone and determine how many digestions they have experienced in any given day. The daily digestion count summary chart 806B shows trends in the daily digestion count metric over time.

The user dashboard 800 further includes a percentage of target goal indicator 808A (FIG. 8A) and a percentage of target goal summary chart 808B (FIG. 8B). The percentage of target goal indicator 808A provides the user with a single number indicative of where they stand with respect to their target number of digestions for the day. For example, the example percentage of target goal indicator 808A in FIG. 8A shows that the user has currently experienced 127% of their target for number of digestion events per day, which indicates to the user that they have ingested too much food and should not eat any more food. The percentage of target goal summary chart 808B plots the daily digestion count ($D_{Total}$) versus time for a given time period, normally 24 hours. Target goal summary chart 808B can also include an interpolated feeding "flight path" for the day. The plot of the daily digestion count can then be compared to the "flight path" for the day. The flight path is an indicator of the desired number of digestions that should have occurred for the user up to any given point in the day. The flight path may be a straight line extending from 0 digestions at 0 hours to the daily goal number of digestions at 24 hours. The flight path could also be curvilinear, allowing for a larger digestion rate at certain parts of the day and a smaller digestion rate at other parts of the day. The flight path could take into account expected meals and have increases in the expected number of digestions following breakfast, lunch, or dinner. The system can also learn from the user and determine a normal flight path for the user during the calibration period. The daily digestion count can then be compared to the determined flight path that is specific to the user.

Summary chart 808B generally has three zones: (1) "Above Target Zone," (2) "In Target Zone," and (3) "Below Target Zone." These zones may be separated by lines or borders that are predetermined by the user's personal upper and lower limit digestion goals. These zones can also be differentiated by some other characteristic, such as color or back ground pattern/design. For example, an individual may seek to maintain their digestion at less than 10,000 digestion events per day, but above 5,000 per day. Once those targets are set, the system linearly extrapolates a "Target Zone" for digestion for the day, assuming the user begins at 0 events at 12:00 AM. If the user wears the device throughout the day, including at night, then the system can track $D_{Total}$ dynamically and determine whether it falls within the extrapolated target zone for digestion. Generally, the extrapolated target zones at any given time during the day are based on predetermined percentages of the user's flight path. For example, if the flight path for a user suggests that the user should have undergone 3,000 digestion events by 12 PM, the "Target Zone" may extend from 2,900 digestion events to 3,100 digestion events. A user who has experienced 5,000 digestions events at 12 PM would thus fall into the "Above Target Zone" region. As the flight path for the user generally increases throughout the day, the target zone will gradually adjust. For example, the same user may have still only have experienced 5,000 digestion events by 3 PM. While 5,000 digestion events may have been above the target zone at 12 PM, 5,000 digestion events could fall into the target zone for that user at 3 PM. Thus, summary chart 808B is dynamically updated throughout the day to provide the user with real-time monitoring of their digestion for the day and how closely it is tracking their desired digestion.

According to some embodiments, the bedside computer or other processing device used to analyze the IR data is configured to display the individualized feeding guidance and the information in user dashboard 800 on an internal display. Additionally, or alternatively, the processor performing the IR analysis can be communicatively coupled to a display device, such as a bedside patient monitoring display. In some embodiments, the feeding guidance and information in user dashboard 800 can be displayed on a monitor used to track other user data, such as heart rate, blood pressure, and other vitals. In still other embodiments, the reporting data may be sent to an external computing device, such as a personal computer, a tablet device, a laptop, a mobile device such as a mobile telephone or a smartphone, or shared across multiple devices capable of receiving reports or information. As yet another alternative, reports can be provided in email, text message, webpage, or other formats and transmitted to one or more devices capable of receiving such messaging.

In some implementations, the display upon which user dashboard 800 is shown can be a touch screen, or can include a number of physical input devices, such as a computer mouse, a keyboard, a track ball, or physical buttons. In some implementations, the user may access the summary charts 802B, 804B, 806B, 808B by selecting the corresponding gauge or indicator 802A, 804A, 806A, 808A within the user dashboard using the touch screen or using the number of physical input devices.

The present disclosure can play an important role in improving the timing of food ingestion to improve human health. Notably, it may also be used for veterinary health to optimize the timing of feeding for animals. The current approach to optimizing food ingestion is limited by non-standardized and imperfect methods. But the methods disclosed herein provide the capability to prospectively optimize the timing of food ingestion in a manner that is physiologically appropriate and may improve health.

Each of these embodiments and obvious variations thereof is contemplated as falling within the spirit and scope of the present disclosure. Moreover, the present concepts expressly include any and all combinations and subcombinations of the preceding elements and aspects.

To provide aspects of the present disclosure, embodiments may employ any number of programmable processing devices that execute software or stored instructions. Physical processors and/or machines employed by embodiments of the present disclosure for any processing or evaluation may include one or more networked (Internet, cloud, WAN, LAN, satellite, wired or wireless (RF, cellular, Wi-Fi, Bluetooth®, etc.)) or non-networked general purpose computer systems, microprocessors, field programmable gate arrays (FPGAs), digital signal processors (DSPs), micro-controllers, smart devices (e.g., smart phones), computer tablets, handheld computers, and the like, programmed according to the teachings of the exemplary embodiments. In addition, the devices and subsystems of the exemplary embodiments can be implemented by the preparation of application-specific integrated circuits (ASICs) or by interconnecting an appropriate network of conventional component circuits. Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, database management software, and the like. Computer code devices of the exemplary embodiments can include any suitable interpretable or executable code mechanism, including but not limited to scripts, interpretable programs, dynamic link libraries (DLLs), Java classes and applets, complete executable programs, and the like. Moreover, processing capabilities may be distributed across multiple processors for better performance, reliability, cost, or other benefit.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method for optimizing timing of food ingestion by a user, the method performed by a computing device and comprising:
   receiving acoustic data from one or more sensors communicatively coupled to the computing device, the one or more sensors including a microphone, each of the one or more sensors being in contact with the user and configured to capture acoustic data from an abdominal region of the user;
   analyzing, via at least one processor of the computing device, the acoustic data received from the one or more sensors to determine a value of each of a plurality of digestive metrics derived from intestinal rate measurements;
   determining, via the at least one processor, an optimal action related to food ingestion based on the values of the plurality of digestive metrics; and
   displaying, via a display device communicatively coupled to the at least one processor, a user dashboard comprising information indicative of the optimal action related to food ingestion,
   wherein the displayed information includes individualized feeding guidance updated based on the determined values of the plurality of digestive metrics that are continually updated, the individualized feeding guidance comprising:
      an indication of whether the user should continue eating;
      an indication of whether the user should stop eating;
      an indication of whether the user should start eating; and
      an indication of whether the user should continue to not eat.

2. The method of claim 1, wherein one of the one or more digestive metrics comprises a measure of a current intestinal rate or a running average of an intestinal rate.

3. The method of claim 2, wherein the measure of the current intestinal rate comprises a number of digestion events experienced during a time period of one minute.

4. The method of claim 2, wherein the running average of the intestinal rate is based on acoustic data analyzed during a time period of twenty minutes and is expressed as a percentage of a maximum intestinal rate.

5. The method of claim 1, wherein the one or more digestive metrics comprises a food tank metric comprising a running average of the user's intestinal rate, the food tank metric being divided into a plurality of zones.

6. The method of claim 5, wherein the food tank metric is divided into a plurality of zones including a first zone, a second zone, and a third zone.

7. The method of claim 6, wherein the user dashboard includes individualized feeding guidance indicating that it is okay to eat or the user should continue eating when the food tank metric is in the first zone.

8. The method of claim 7, wherein the user dashboard includes individualized feeding guidance indicating that the user should think about stopping eating or not starting eating when the food tank metric is in the second zone.

9. The method of claim 8, wherein the user dashboard includes individualized feeding guidance indicating that the user should stop eating or should not start eating when the food tank metric is in the third zone.

10. The method of claim 1, wherein one of the one or more digestive metrics comprises a measure of a total number of digestive events experienced during a time period.

11. The method of claim 10, wherein one of the one or more digestive metrics comprises a ratio of the total number of digestive events experienced during the time period to a goal number of digestive events for the time period.

12. The method of claim 11, wherein the time period is one day.

13. The method of claim 1, wherein:
   the displayed user dashboard further comprises a summary of at least two of the plurality of digestive metrics;
   the at least two digestive metric comprises a food tank metric and a percentage of target goal metric;
   the food tank metric is a measure of how full the user's intestine is based on a running average of the user's intestinal rate;
   the percentage of target goal metric is a measure of a percentage of a targeted number of daily digestions achieved up until the current time;
   each of the food tank metric and the target goal metric is divided into a plurality of categories; and
   categories of the food tank metric and percentage of target goal metric included in the user dashboard are updated in real-time based on values of the food tank metric and percentage of target goal metric that are continually updated.

14. The method of claim 1, further comprising measuring acoustic data during a calibration period to determine (i) a maximum post-meal intestinal rate during the calibration period and (ii) a total number of digestions experienced during the calibration period.

15. The method of claim 14, wherein the optimal action related to food ingestion is based on a target number of digestions for the time period.

16. The method of claim 15, wherein a ratio of the target number of digestions for the time period to the average number of digestions for the time period is less than one.

17. The method of claim 10, further comprising displaying, via the display device, a comparison between the total number of digestive events experienced during the time period and a goal number of digestive events for the time period.

18. A system for optimizing timing of food ingestion by a user, the system comprising:
   a sensor device having a base portion and an acoustic sensor including a microphone, the acoustic sensor being coupled to the base portion via an extendible member and contacting an abdominal region of the user, the acoustic sensor being configured to capture acoustic data from the abdominal region of the user during a calibration period, a first time period, and a second time period; and
   a computing device communicatively coupled to the sensor device and comprising:
      a processing device configured to receive the acoustic data from the sensor device, the processing device further being configured to analyze the acoustic data to determine (i) a maximum post-meal intestinal rate during the calibration period and a total number of digestions experienced during the calibration period (ii) a maximum post-meal intestinal rate during the first time period and a total number of digestions experienced during the first time period, and (iii) a running average of an intestinal rate during the second time period and a current number of digestions experienced during the second time period; and a display device communicatively coupled to the processing device, the display device being configured to display a user dashboard comprising information indicative of an optimal action related to food ingestion based on (i) a first ratio of (a) the running average of the intestinal rate during the second time period to (b) the maximum post-meal intestinal rate during the first time period, and (ii) a second ratio of (a) the current number of digestions experienced during the second time period to (b) the total number of digestions experienced during the first time period, wherein the displayed information includes individualized feeding guidance updated based on the first ratio and the second ratio that are continually updated, the individualized feeding guidance comprising:

an indication of whether the user should continue eating;

an indication of whether the user should stop eating;

an indication of whether the user should start eating; and an indication of whether the user should continue to not eat.

19. A method for optimizing timing of food ingestion by a user, the method performed by a system comprising a computing device and a sensor device communicatively coupled to the computing device, and the method comprising:

measuring, via the sensor device with an acoustic sensor including a microphone, acoustic data from the user during a calibration period;

analyzing, via at least one processor of the computing device, the acoustic data received from the sensor device via a communication module to determine (i) a maximum post-meal intestinal rate during the calibration period and (ii) a total number of digestions experienced during the calibration period;

measuring, via the sensor device, first acoustic data from the user during a first time period;

analyzing, via the at least one processor, the first acoustic data received from the sensor device to determine (i) a maximum post-meal intestinal rate during the first time period and (ii) a total number of digestions experienced during the first time period;

measuring, via the sensor device, second acoustic data from the user during a second time period;

analyzing, via the at least one processor, the second acoustic data received from the sensor device to determine (i) a running average of an intestinal rate during the second time period and (ii) a current number of digestions experienced during the second time period; and providing, via a display device of the computing device, information indicative of an optimal action related to food ingestion during the second time period based on (i) a first ratio of (a) the running average of the intestinal rate during the second time period to (b) the maximum post-meal intestinal rate during the first time period, and (ii) a second ratio of (a) the current number of digestions experienced during the second time period to (b) the total number of digestions experienced during the first time period, wherein the displayed information includes individualized feeding guidance updated based on the first ratio and the second ratio that are continually updated, the individualized feeding guidance comprising:

an indication of whether the user should continue eating;

an indication of whether the user should stop eating;

an indication of whether the user should start eating; and an indication of whether the user should continue to not eat.

* * * * *